US00PP27974P2

(12) United States Plant Patent
Miyazaki

(10) Patent No.: US PP27,974 P2
(45) Date of Patent: May 2, 2017

(54) ***LOBELIA* PLANT NAMED 'SUNLOBE TORECAMA'**

(50) Latin Name: *Lobelia erinus*
Varietal Denomination: Sunlobe Torecama

(71) Applicant: SUNTORY FLOWERS LIMITED, Tokyo (JP)

(72) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 14/998,340

(22) Filed: Jan. 4, 2016

(51) Int. Cl.
*A01H 5/02* (2006.01)

(52) U.S. Cl.
USPC ..... Plt./451

(58) Field of Classification Search
USPC ..... Plt./451
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Lobelia* plant named 'Sunlobe Torecama', characterized by its upright to trailing and mounding plant habit; vigorous growth habit; freely branching habit; dense and bushy plant form; freely flowering habit; long flowering period; large purple violet-colored flowers with white-colored centers; relative tolerance to high temperatures and good garden performance.

1 Drawing Sheet

Botanical designation: *Lobelia erinus.*
Cultivar denomination: 'SUNLOBE TORECAMA'.

BACKGROUND OF THE INVENTION

The present invention relates to a new and distinct cultivar of *Lobelia* plant, botanically known as *Lobelia erinus* and hereinafter referred to by the name 'Sunlobe Torecama'.

The new *Lobelia* plant is a product of a planned breeding program conducted by the Inventor in Higashiomi, Shiga, Japan. The objective of the breeding program is to create new outwardly spreading to trailing *Lobelia* plants with large attractive flowers, good garden performance and high temperature tolerance.

The new *Lobelia* plant originated from a cross-pollination made by the Inventor in May, 2012 of a proprietary selection of *Lobelia erinus* identified as code number 11Lob-16a, not patented, as the female, or seed, parent with a proprietary selection of *Lobelia erinus* identified as code number 11Lob-16b, not patented, as the male, or pollen, parent. The new *Lobelia* plant was discovered and selected by the Inventor as a single flowering plant within the progeny of the stated cross-pollination in a controlled greenhouse environment in Higashiomi, Shiga, Japan in May, 2013.

Asexual reproduction of the *Lobelia* plant by vegetative cuttings in Higashiomi, Shiga, Japan since May, 2013 has shown that the unique features of this new *Lobelia* plant are stable and reproduced true to type in successive generations.

SUMMARY OF THE INVENTION

Plants of the new *Lobelia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunlobe Torecama'. These characteristics in combination distinguish 'Sunlobe Torecama' as a new and distinct *Lobelia* plant:

1. Upright to trailing and mounding plant habit.
2. Vigorous growth habit.
3. Freely branching habit; dense and bushy plant form.
4. Freely flowering habit.
5. Long flowering period.
6. Large purple violet-colored flowers with white-colored centers.
7. Relatively tolerant to high temperatures.
8. Good garden performance.

Plants of the new *Lobelia* differ primarily from plants of the female parent selection in branching habit as plants of the new *Lobelia* are more freely branching than plants of the female parent selection.

Plants of the new *Lobelia* differ primarily from plants of the male parent selection in flower size as plants of the new *Lobelia* have larger flowers than plants of the male parent selection.

Plants of the new *Lobelia* can be compared to plants of *Lobelia erinus* 'Lobmounlila' , disclosed in U.S. Plant Pat. No. 18,410. In side-by-side comparisons conducted in Higashiomi, Shiga, Japan, plants of the new *Lobelia* differed from plants of 'Lobmounlila' in the following characteristics:

1. Plants of the new *Lobelia* were more trailing than and not as upright as plants of 'Lobmounlila'.
2. Plants of the new *Lobelia* were taller and broader than plants of 'Lobmounlila'.
3. Leaves of plants of the new *Lobelia* were longer and narrower than leaves of plants of 'Lobmounlila'.
4. Flowers of plants of the new *Lobelia* had larger centers than flowers of plants of 'Lobmounlila'.

5. Plants of the new *Lobelia* were more high temperature tolerant than plants of 'Lobmounlila'.

BRIEF DESCRIPTION OF THE PHOTOGRAPHS

The accompanying colored photographs illustrate the overall appearance of the new *Lobelia* plant showing the colors as true as it is reasonably possible to obtain in colored reproductions of this type. Colors in the photographs may differ slightly from the color values cited in the detailed botanical description which accurately describe the actual colors of the new *Lobelia* plant.

The photograph at the top of the sheet comprises a side perspective view of a typical flowering plant of 'Sunlobe Torecama' grown in a container.

The photograph at the bottom of the sheet is a close-up view of a typical flowering plant of 'Sunlobe Torecama'.

DETAILED BOTANICAL DESCRIPTION

Plants used for the aforementioned photographs and following description were grown in 15-cm containers during the spring and early summer in an outdoor nursery in Higashiomi, Shiga, Japan and under cultural practices typical of commercial *Lobelia* production. During the production of the plants, day temperatures averaged 23° C. and night temperatures averaged 13° C. Plants were four months old when the photographs and description were taken. In the following description, color references are made to The Royal Horticultural Society Colour Chart, 2007 Edition, except where general terms of ordinary dictionary significance are used.

Botanical classification: *Lobelia erinus* 'Sunlobe Torecama'.

Parentage:

*Female, or seed, parent*.—Proprietary selection of *Lobelia erinus* identified as code number 11Lob-16a, not patented.

*Male, or pollen, parent*.—Proprietary selection of *Lobelia erinus* identified as code number 11Lob-16b, not patented.

Propagation:

*Type cutting*.—Vegetative cuttings.

*Time to initiate roots, summer and winter*.—About one week at temperatures about 15° C. to 20° C.

*Time to produce a rooted young plant, summer and winter*.—About three weeks at temperatures about 15° C. to 20° C.

*Root description*.—Fibrous; typically white in color, actual color of the roots is dependent on substrate composition, water quality, fertilizer type and formulation, substrate temperature and physiological age of roots.

*Rooting habit*.—Freely branching; relatively dense.

Plant description:

*Plant and growth habit*.—Upright to trailing and mounding plant habit; freely branching habit with lateral branches developing at potentially every node; dense and bushy plant habit; vigorous growth habit.

*Plant height*.—About 25 cm.

*Plant width*.—About 65 cm.

*Lateral branch description*.—Length: About 24 cm to 29 cm. Diameter: About 1.3 mm to 1.6 mm. Internode length: About 2.3 cm. Strength: Strong, flexible. Aspect: Outwardly spreading. Texture: Smooth, glabrous. Color: Close to 137B.

Leaf description:

*Arrangement*.—Alternate, simple; sessile.

*Length*.—About 3.3 cm.

*Width*.—About 5.4 mm.

*Shape*.—Lanceolate to oblong.

*Apex*.—Acute.

*Base*.—Cuneate.

*Margin*.—Shallowly serrate.

*Texture and luster, upper and lower surfaces*.—Smooth, glabrous; matte.

*Venation pattern*.—Pinnate.

*Color*.—Developing leaves, upper surface: Close to N137D. Developing leaves, lower surface: Close to 137C. Fully expanded leaves, upper surface: Close to N137C; venation, close to 138B. Fully expanded leaves, lower surface: Close to 137C; venation, close to 138B.

Flower description:

*Flower arrangement, habit and shape*.—Flowers typically arranged in terminal and lateral racemes; flowers face mostly outwardly to slanting downward; freely flowering habit with about five flowers per inflorescence and more than 500 flowers developing per plant; flowers bilabiate with two upper petals and three larger lower petals.

*Fragrance*.—None detected.

*Natural flowering season*.—In Japan, plants of the new *Lobelia* flower continuously from May until October; early flowering habit, plants begin flowering about three to four weeks after planting.

*Flower longevity on the plant*.—Longevity of individual flowers is highly dependent on temperature, flowers typically last about 10 to 14 days on the plant; flowers persistent.

*Inflorescence length*.—About 16.4 cm.

*Inflorescence diameter*.—About 10.6 cm.

*Flower length*.—About 1.5 cm.

*Flower diameter*.—About 1.6 cm.

*Flower depth*.—About 1.5 cm.

*Flower tube length*.—About 7 mm.

*Flower tube diameter, mid-section*.—About 2.6 mm.

*Flower tube diameter, base*.—About 1.6 mm.

*Flower throat diameter*.—About 3.5 mm.

*Flower buds*.—Length: About 1.2 cm. Diameter: About 3.3 mm. Shape: Club-shaped. Color: Towards the apex, close to 77A; mid-section, close to 145C; towards the base, close to N80B.

*Petals*.—Arrangement: Single whorl of five petals fused towards the base; two upper petals and three larger lower petals. Upper petals: Length, beyond throat: About 5.3 mm. Width: About 1.7 mm. Shape: Elliptic. Apex: Acute. Margin: Entire. Texture and luster, upper and lower surfaces: Smooth, glabrous; matte. Lower petals: Length, central petal, beyond throat: About 9.7 mm. Length, lateral petals, beyond throat: About 9.1 mm. Width, central petal, beyond throat: About 5 mm. Width, lateral petals, beyond throat: About 6 mm. Shape, central and lateral petals: Obovate. Apex, central and lateral petals: Cuspidate. Margin, central and lateral petals: Entire; slightly undulate. Texture and luster, central and lateral petals, upper and lower surfaces: Smooth, glabrous; matte. Color, upper petals: When opening and fully opened, upper surface: Close to N81A. When opening and fully opened, lower surface: Close to N81B.

Color, lower petals: When opening and fully opened, upper surface: Close to N81A; towards the throat, close to NN155D. When opening and fully opened, lower surface: Close to N81B; towards the throat, close to NN155D. Color, throat: Close to 84B; spots, close to N81B; nectar guides, close to 144D. Color, tube: Close to N81B.

*Sepals*.—Arrangement: Single whorl of five sepals, fused at the base; star-shaped calyx. Length: About 4.4 mm. Width: About 0.9 mm. Shape: Lanceolate. Apex: Acute. Margin: Entire. Texture and luster, upper and lower surfaces: Smooth, glabrous; matte. Color, upper and lower surfaces: Close to 137B tinged with close to 79B.

*Pedicels*.—Length: About 1.8 cm. Diameter: About 0.4 mm. Strength: Strong, flexible. Texture: Smooth, glabrous. Color: Close to 143A.

*Reproductive organs*.—Stamens: Quantity per flower: Five. Filament length: About 5.7 mm. Filament color: Distally, close to N82A; proximally, close to N82D. Anther size: About 1 mm by 1.5 mm. Anther shape: Elliptic. Anther color: Close to 72A. Pollen amount: Moderate. Pollen color: Close to 4C. Pistils: Quantity per flower: One. Pistil length: About 8.2 mm. Stigma shape: Globose. Stigma color: Close to 92A. Style color: Close to N82B. Ovary color: Close to 145B.

*Fruits and seeds*.—Fruit and seed development have not been observed on plants of the new *Lobelia*.

Disease & pest resistance: Plants of the new *Lobelia* have not been noted to be resistant to pathogens and pests common to *Lobelia* plants.

Garden performance: Plants of the new *Lobelia* have been observed to have good garden performance and to tolerate wind, rain and temperatures ranging from about 5° C. to about 35° C.

It is claimed:

1. A new and distinct *Lobelia* plant named 'Sunlobe Torecama' as illustrated and described.

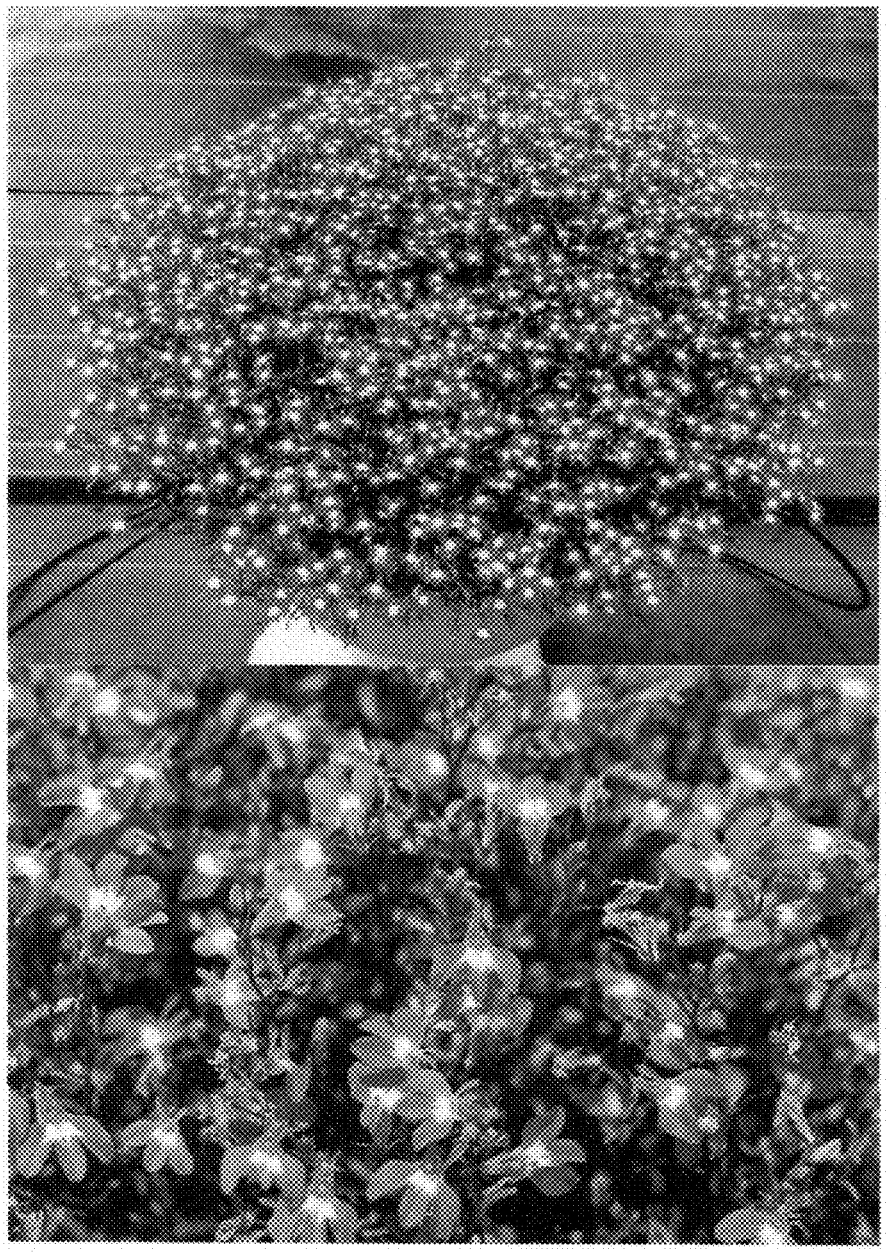

* * * * *